United States Patent [19]

Comins

[11] Patent Number: 5,496,952
[45] Date of Patent: Mar. 5, 1996

[54] METHOD OF MAKING ASYMMETRIC DE RING INTERMEDIATES FOR THE SYNTHESIS OF CAMPTOTHECIN AND CAMPTOTHECIN ANALOGS

[75] Inventor: Daniel L. Comins, Cary, N.C.

[73] Assignee: North Carolina State University, Raleigh, N.C.

[21] Appl. No.: 384,758

[22] Filed: Feb. 7, 1995

[51] Int. Cl.[6] .................... C07D 491/052; C07D 213/55
[52] U.S. Cl. ............................................. 546/116; 546/342
[58] Field of Search .................................... 546/116, 342

[56] References Cited

U.S. PATENT DOCUMENTS

| | | | |
|---|---|---|---|
| 4,578,381 | 3/1986 | Uchida et al. | 514/233 |
| 4,894,456 | 1/1990 | Wall et al. | 546/41 |
| 5,162,532 | 11/1992 | Comins et al. | 546/48 |
| 5,191,082 | 3/1993 | Comins et al. | 546/116 |
| 5,212,317 | 5/1993 | Comins et al. | 546/301 |
| 5,243,050 | 9/1993 | Comins et al. | 546/116 |
| 5,342,947 | 8/1994 | Lackey et al. | 546/41 |

FOREIGN PATENT DOCUMENTS

| | | |
|---|---|---|
| 0325247 | 7/1989 | European Pat. Off. . |
| 0540099 | 5/1993 | European Pat. Off. . |
| WO94/11377 | 5/1994 | WIPO . |

OTHER PUBLICATIONS

Comins, D. L., et al., *Lithiation of Methoxypyridines Directed by α-Amino Alkoxides*, The Journal of Organic Chemistry, 55 (1) p. 69 (1990).

Comins, D. L., *Ortho Lithiation of 2-,3-, and 4-Methoxypyridines*, Tetrahedron Letters, 29 (7) p. 773 (1988).

Lyle, R. E., et al., *Synthetic Approaches to Camptothecin*, Abstracts, 23rd International Congress of Pure and Applied Chemistry, Abstracts, p. 67 (1971).

Lyle, R. E., et al., *The Synthesis of an Analog of Camptothecin by a General Method*, The Journal of Organic Chemistry, 38 (19) p. 3268 (1973).

Comins, D. L., et al., *Ortho Metalation Directed by α-Amino Alkoxides*, The Journal of Organic Chemistry, 49: p. 1078 (1984).

Comins, D. L., et al., *Ortho Substitution of m-Anisaldehyde via α-Amino Alkoxide Directed Lithiation*, The Journal of Organic Chemistry, 54: p. 3730 (1989).

Bristol, J. A., et al., *Analogs of Camptothecin*, The Journal of Medicinal Chemistry, 18 (5) p. 535 (1975).

Abramovitch, *Pyridine and Its Derivatives, Heterocyclic Compounds*, Suppl. Pt. 3., 14: p. 745 (1982).

Sugasawa, T., et al., *Experiments on the Synthesis of dl–Camptothecin. II.–Synthesis of a D–E Ring Analog of Camptothecin and a Total Synthesis of Ricinine*, Chem. Pharm. Bull., 22 p. 763 (1974).

Plattner, J. J., et al., *Synthesis of Some DE and CDE Ring Analogs of Camptothecin*, The Journal of the American Chemical Society, 94:24: p. 8613 (1972).

Cai, J. *Camptothecin*, The Alkaloids, 21 p. 101 (1983).

Comins, D. L., *A 10–Step Asymmetric Synthesis of (S)–Campothecin*, Journal of the American Chemical Society, p. 10971 (1992).

Comins, D. L., Ph.D. *Thesis*, University of New Hampshire, Durham, New Hampshire pp. 25–29 (1977).

Lyle, Robert E. et al; *Benzylic Halogenation of Methylquinolines*, The Journal of Organic Chemistry 37 (24) p. 3967 (1972).

Grigg, R, et al; *The Synthesis of Fused Ring Introgen Heterocycles VIA Regiospecific Intramolecular Heck Reactions* Tetrahedron 46 (11) p. 4003 (1990).

Larlock, Richard C.; *Comprehensive Organic Transformations* VCH Publishers pp. 501–504 (1989).

Rocca, P.; *First Metalation of Aryl Iodides: Directed Ortho–Lithiation of Iodopyridines, Halogen–Dance, and Application to Synthesis*, J. Org. Chem., 58 p. 7832 (1993).

Primary Examiner—Bernard Dentz
Attorney, Agent, or Firm—Bell, Seltzer, Park & Gibson

[57] ABSTRACT

The present invention is directed towards new methods of making DE ring intermediates of Formula (III),

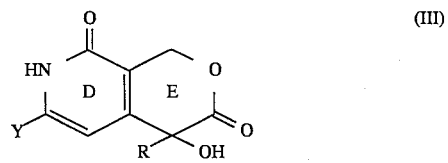

wherein Y is H or halogen and R is loweralkyl,
which in turn are useful in methods of making camptothecin and camptothecin analogs. The present invention also provides new compounds useful in the methods of making compounds of Formula (III).

22 Claims, No Drawings

METHOD OF MAKING ASYMMETRIC DE RING INTERMEDIATES FOR THE SYNTHESIS OF CAMPTOTHECIN AND CAMPTOTHECIN ANALOGS

FIELD OF THE INVENTION

The present invention provides methods for making asymmetric DE ring intermediates in optically pure form via 2-fluoropyridine intermediates.

BACKGROUND OF THE INVENTION

Camptothecin (Chem. Abstracts Registry No. 7689-03-4) is a naturally occurring compound found in *Camptotheca acuminata* (Nyssaceae) which has antileukemic and antitumor properties. Numerous camptothecin analogs having like properties are known, examples being those described in U.S. Pat. No. 4,894,456 to Wall et al. and European Patent Application No. 0 325 247 of Yaegashi et al.

A number of syntheses for camptothecin are known. Several routes are reviewed in *Natural Products Chemistry*, Vol. 2, 358–361 (K. Nakanishi, T. Goto, S. Itô, S. Natori and S. Nozoe eds.) and in J. Cai and C. Hutchinson, Camptothecin, in *The Alkaloids*, Vol. XXI, 101–137 (Academic Press 1983). The biosynthesis of camptothecin is described in *Natural Products Chemistry*, Vol. 3, 573–574 (K.Nakanishi et al. eds.). One synthetic route is described in U.S. Pat. No. 4,894,456 to Wall et al.

U.S. Pat. No. 5,162,532 to Comins and Baevsky describes a parallel synthesis for camptothecin and camptothecin analogs, where compounds of Formula I are prepared by scheme A:

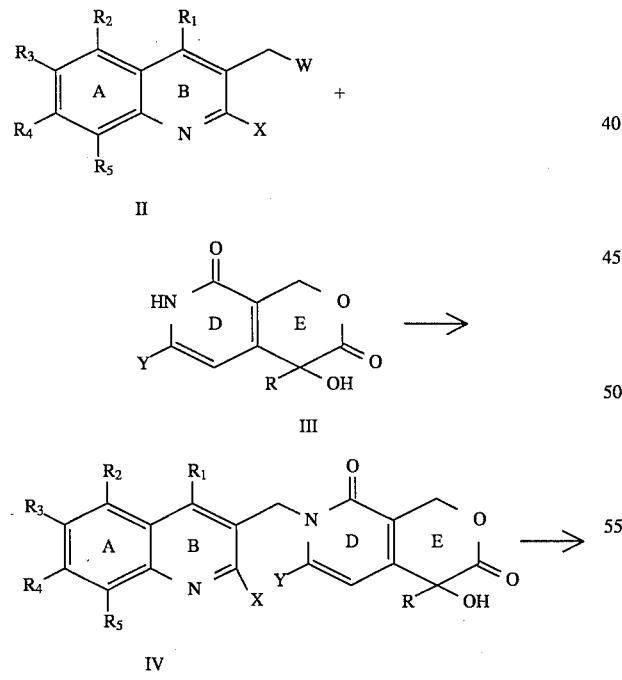

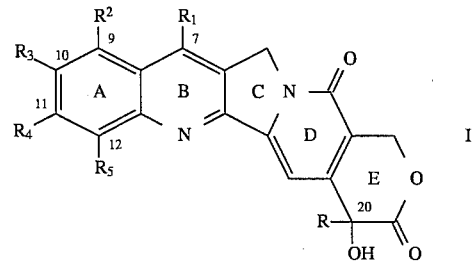

In U.S. Pat. No. 5, 212,317 to Comins and Baevsky, compounds of Formula III in scheme A above are prepared in asymmetric form in accordance with scheme C below:

Scheme C

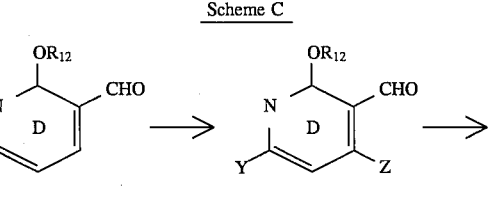

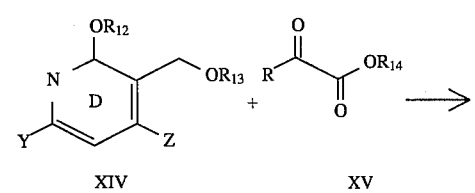

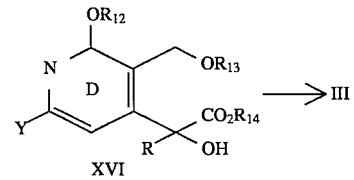

An object of the present invention is to provide new methods for preparing compounds of Formula III above and useful for making such compounds, all of which are useful for the synthesis of camptothecin and camptothecin analogs.

SUMMARY OF THE INVENTION

The present invention provides methods and intermediates for preparing compounds of Formula III:

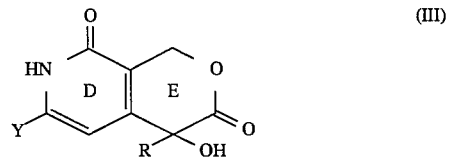

(III)

wherein R is loweralkyl, and Y is H or halogen.

In one embodiment, illustrated by Scheme D,

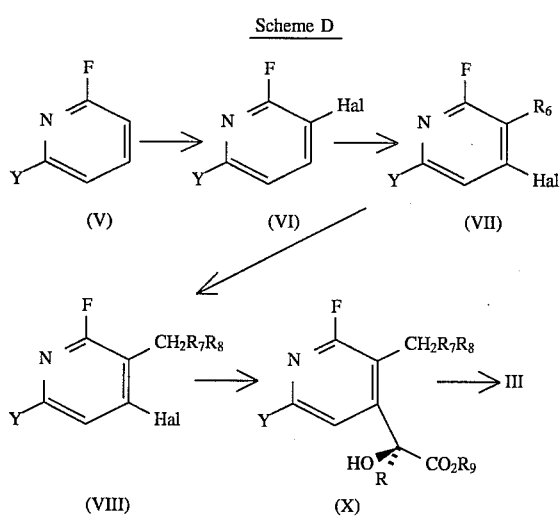

Scheme D (V) → (VI) → (VII) → (VIII) → (X) → III $R_9$ is optically pure, which can lead to a diastereomerically enhanced compound (X) and optically pure compounds of Formula (III).

In an alternate embodiment of the present invention, compounds of Formula III may be prepared according to the following Scheme E,

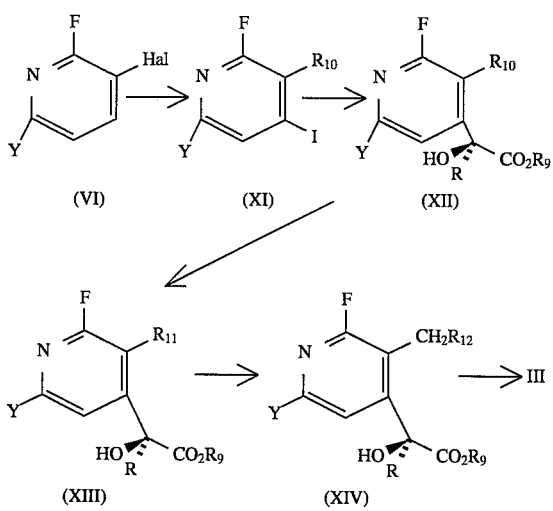

Scheme E (VI) → (XI) → (XII) → (XIII) → (XIV) → III

In Scheme E, $R_9$ is optically pure, and can lead to diastereomerically enhanced compounds of Formula (XII), (XIII), and (XIV) and optically pure compounds of Formula (III).

The foregoing and other objects and aspects of the present invention are explained in detail in the specification set forth below.

DETAILED DESCRIPTION OF THE INVENTION

As used herein, the term "loweralkyl" means a linear or branched alkyl group with 1-8, preferably 1-4 carbon atoms, such as methyl, ethyl, propyl, isopropyl, n-butyl, tert-butyl, hexyl, and octyl. This definition also applies to a loweralkyl moiety in the loweralkoxy, loweralkylhydroxy, loweralkylthio, and di(loweralkyl)amino groups. Thus, examples of loweralkyoxy groups are methoxy, ethoxy, propoxy, sec-butoxy, and isohexoxy; examples of loweralkylthio groups are methylthio, ethylthio, tert-butylthio, and hexylthio; and examples of di(loweralkyl)amino groups are dimethylamino, diethylamino, diisopropylamino, di(n-butyl)amino, and dipentylamino.

The terms "halo" and "halogen" as used herein refers to a substituent which may be fluoro, chloro, bromo, or iodo.

As noted above, compounds of Formula (III) may be prepared according to new methods. One new method is illustrated in Scheme D.

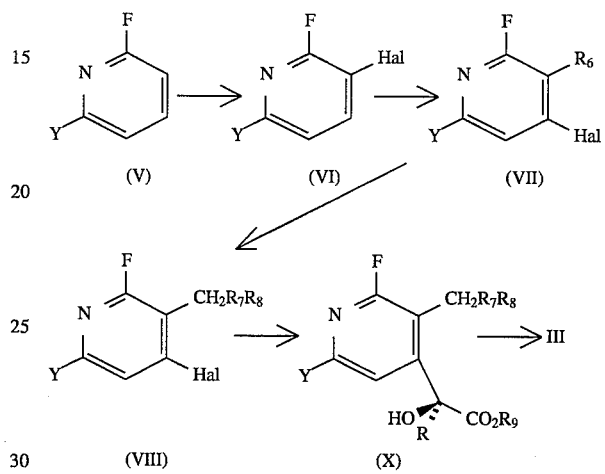

Scheme D (V) → (VI) → (VII) → (VIII) → (X) → III wherein Y is H or halogen, Hal is halogen, $R_6$ is loweralkylhydroxy, $R_7$ is loweralkoxy, $R_8$ is loweralkoxy, and R is loweralkyl. $R_9$ can be any chiral moiety which, because of its geometric configuration, directs the nucleophilic substitution of compound (VIII) by compound (IX) to preferentially form the tertiary alcohol of compound (X) in one stereochemical orientation over its opposite stereochemical orientation. $R_9$ forces a preferential formation of compound (X) by sterically hindering the competing formation of the nonpreferred diastereomer. Exemplary chiral compounds suitable for use in the process include aryl and alkyl aryl compounds optionally substituted from 1 to 5 times with $C_{1-4}$ alkyl groups, any of the compounds disclosed in U.S. Pat. No. 5,262,571 issued 16 Nov. 1993, the subject matter of which is incorporated herein by reference, 4-phenylmethyl-2-oxazolidone, 3-(1-naphthyl)-4,7,7-trimethyl-bicyclo[2.2.1]heptane, trans-2,5-bis(methoxymethoxymethyl)pyrrolidine, 2,10-camphorsultam, proline benzyl ester, pantolactone, and 4-benzyl-Z-oxazolidinone. Preferred chiral auxiliaries are set forth in detail below.

Scheme D begins with the commercially available fluoropyridines of Formula (V). The fluoropyridine of Formula (V) is halogenated to produce the halopyridines of Formula (VI). Halogenation at the number 3 position may be accomplished by reacting the fluoropyridine of Formula (V) with lithium diisopropylamide (LDA) and a halogen, such as $Br_2$, and $I_2$. The reaction is carried out at a temperature of below $-50°$ C., and preferably from about $-50°$ C. to about $-78°$ C. Preferably this step is carried out in an aprotic solvent, such as tetrahydrofuran, diethyl ether, dimethoxyethane, and toluene, with tetrahydrofuran being preferred.

The resulting compound of Formula (VI) is substituted at the number 3 position and halogenated to produce the compound of Formula (VII). The substitution of the number 3 position and halogenation of the number 4 position may be accomplished by reacting the compound of Formula (VI)

with LDA and ethyl formate in an aprotic solvent, such as those described above, in particular, tetrahydrofuran. The reaction is carried out at a temperature of at least as low as about −70° C. The intermediate is further reacted with sodium borohydride to produce the compound of Formula (VII).

The compound of Formula (VII) is alkylated with diisopropylethylamine, dimethylaminopyridine and chloromethylmethyl ether to produce the compound of Formula (VIII). Alkylation of the loweralkylhydroxy at position 3 is preferably carried out in a halogenated solvent, such as methylene chloride, at a temperature of about 0 ° C.

The compound of Formula (VIII) is dehalogenated with a base of the formula $A^+B^-$, wherein $A^+$ is an inorganic cation, and $B^-$ is an organic anion, to form an intermedieate. The intermediate is then reacted with an α-ketoester of Formula (IX)

wherein R and $R_9$ are as defined above, to form the compound of Formula (X).

The base $A^+B^-$ can be any combination of an inorganic cation and an organic anion which will remove the halo group from compound (VIII) to form a reactive carbanion intermediate. Exemplary inorganic cations include sodium, potassium, and lithium, with lithium being more preferred. The organic anion can be any anion which is sufficiently reactive to remove the halo group from compound (VIII) but is insufficiently strong to remove substituent Y from (VIII). Exemplary organic anions include propyl, n-butyl, phenyl, and n-pentyl, with n-butyl being preferred.

The reaction step in which the halo group is removed from compound (VIII) can be carried out through the use of standard conditions for removing halogens from aromatic compounds. Preferably, this step is carried out in an inert atmosphere, such as argon or nitrogen, and in an aprotic solvent, such as those described above, with tetrahydrofuran being preferred. The reaction is preferably carried out at a reduced temperature, and more preferably is carried out below 0° C.

The combination of the intermediate produced by reaction with base $A^+B^-$ and an α-ketoester of Formula (IX) can be carried out through the use of standard conditions for nucleophilic attack of an aromatic carbanion at an α-carbonyl carbon. Preferably, the reaction is carried out in an aprotic solvent, such as those listed above, with tetrahydrofuran being preferred, and is carried out at a reduced temperature, preferably below 0° C. In a more preferred embodiment of the process, the reacting step and the combining step are carried out in the same reaction vessel, i.e., in situ.

The α-ketoester bears the chiral auxiliary, which because of its geometric configuration, directs the nucleophilic substitution of compound (VIII) by compound (IX) to preferentially form the tertiary alcohol of compound (X) in one stereochemical orientation over its opposite stereochemical orientation. R9 forces a preferential formation of compound (X) by sterically hindering the competing formation of the nonpreferred diastereomer. Exemplary chiral compounds suitable for use in the process include aryl and alkyl aryl compounds optiionally substituted from 1 to 5 times with $C_1$–$C_4$ alkyl groups, any of the compounds disclosed in U.S. Pat. No. 5,262,571 issued 16 Nov. 1993, the subject matter of which is herein incorporated by reference, 4-phenyl-methyl-2-oxazolidine, 3-(1-naphthyl)-4,7,7-trimethyl-bicyclo [2.2.1]heptane, trans-2,5 bis(methoxymethoxymethyl)-pyrrolidine,2,10-camphorsultam, prolinebenzylester, pantolactone, and 4-benzyl-Z-oxazolidinone. Preferred chiral auxiliaries are compounds of Formula

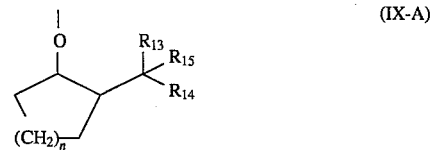

wherein n is 1, 2, or 3, $R_{13}$ is a $C_1$–$C_4$ alkyl group and $R_4$ is the same as $R_3$, or $R_{13}$ and $R_{14}$ together form cyclopentane or cyclohexane, and $R_{15}$ is selected from the group consisting of phenyl, naphthyl, anthryl, and phenanthryl optionally substituted 1 to 5 times with $C_3$–$C_7$ secondary alkyl or $C_4$–$C_7$ tertiary alkyl groups. The position of alkyl substituents on the aryl group is not critical; for example, phenyl can be substituted at positions 1–6, naphthyl from positions 1–8, anthryl from positions 1–10, and phenanthryl from positions 1–10 substituted from 1 to 5 times with $C_1$–$C_4$ alkyl groups. It is understood that the oxygen atom illustrated in Formula (IX-A) links the chiral auxiliary to the carbonyl carbon of the compound of Formula (IX) and is included in Formula (IX-A) to indicate the preferred bonding position of the cyclic alkyl group to the carbonyl carbon. In a more preferred chiral auxiliary, $R_{13}$ and $R_{14}$ are both methyl or ethyl, and $R_{15}$ is phenyl.

In many instances it will be desirable that compound (X) has the stereochemical orientation of Formula (X-A)

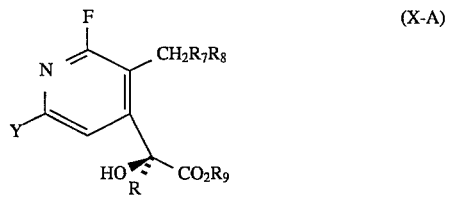

In such instances, $R_9$ should be an optically pure chiral auxiliary that will permit only the formation of diastereomers of compound (X) having this orientation. As used herein, an "optically pure" compound is one which contains at least 99 percent of one enantiomer of that compound. Preferred chiral auxiliaries for forming the distereomers of Formula (IX-A) are as shown in Formula (IX-B)

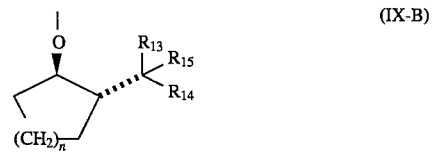

wherein R, $R_{13}$, $R_{14}$, and $R_{15}$ are as defined above for Formula (IX-A). As above, the oxygen atom of compound (IX-B) is included to show bonding position on the cyclic alkyl group and stereochemical orientation of the substitutents thereon.

The final step of Scheme D is the formation of compound III from a compound of Formula (X) by hydrolysis. The chiral auxiliary is removed from the compound of Formula (X), the ether group is cleaved and an ester ring is formed with the linkage at the position previously occupied by the chiral auxiliary. The ether cleavage and ester cyclization reaction may be carried out by hydrolysing the compound of Formula (X) with aqueous dilute inorganic acid. Preferably the inorganic acid is hydrochloric diluted to 10 percent. The reaction is heated at reflux for approximately 36 hours. The reaction may be carried out in a polar solvent, such as methanol, ethanol, isopropanol, etc. Preferably the solvent is methanol. The reaction produces the compounds of Formula (III) in cyrstalline form, having a melting point between about 216°–218° C.

When Y is halo in the compound of Formula (III), the compound may be hydrogenated by any suitable technique, preferably by catalytic hydrogenation in the presence of a palladium catalyst in a hydrogen atmosphere under pressure (e.g., at least three atmospheres). See generally, J. March, *Advanced Organic Chemistry* 510–511 (3d. Ed. 1985).

In an alternate embodiment of the present invention, compounds of Formula (III) are prepared according to Scheme E.

Scheme E

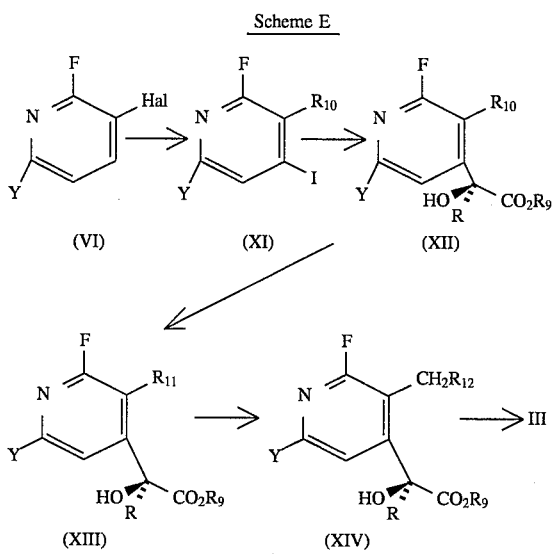

wherein Y is H or halogen, Hal is halogen, $R_{10}$ is loweralkyl, R is loweralkyl, $R_{11}$ is haloalkyl, $R_{12}$ is lowercarboxy or arylcarboxy, and $R_9$ is as defined above in connection with Scheme D.

Scheme E begins with the compounds of Formula (VI) which are prepared as described above. The compounds of Formula (VI) are then substituted at position 3 to produce the compounds of Formula (XI) according to the method of P. Rocca, *J. Org. Chem.* 58:7832 (1993). More particularly, substitution and alkylation of position 3 may be accomplished by reacting the halopyridine of Formula (VI) with LDA and a loweralkyl halogen such as methyl iodide, ethyl iodide, or propyl iodide. The substitution and alkylation is preferably carried out in an aprotic solvent such as tetrahydrofuran, at a temperature below 0° C. and preferably below –20° C.

The compounds of Formula (XI) are then dehalogenated with a base of Formula $A^+B^-$, as described above in connection with the previous method. The intermediate formed is then reacted with an α-ketoester of Formula (IX) to form the compound of Formula (XII). The dehalogenation reaction step proceeds as described above in connection with the previous method of making compounds of Formula (III). Also as described above, preferably the α-ketoester bears the chiral auxiliary, which because of its geometric configuration, directs the nucleophilic substitution of compound (XI) by compound (IX) to preferentially form the tertiary alcohol of compound (XII) in one stereochemical orientation over its opposite stereochemical orientation. The chiral auxiliaries useful in the instant method are described above in connection with Scheme D.

In many instances, it will be desireable that the compounds of Formula (XII) have the stereochemical orientation of Formula (XII-A)

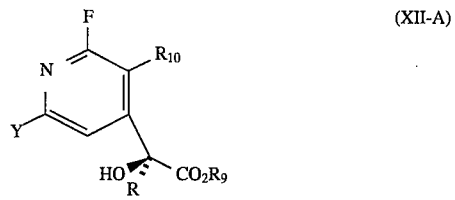

(XII-A)

In such instances, $R_9$ should be an optically pure chiral auxiliary as described above in connection with Scheme D.

The compound of Formula (XII) is then substituted at position 3 with a loweralkylhalo to provide the compounds of Formula (XIII). The substitution reaction may be accomplished by reacting the compound of Formula (XII) with N-bromosuccinimide and dibenzoyl peroxide, in a halogenated solvent such as carbon tetrachloride at reflux. In the embodiment wherein the compound of Formula (XII) is diastereomerically enhanced, the resulting compounds of Formula (XIII) are likewise diastereomerically enhanced, and have the stereochemical orientation of Formula (XIII-A)

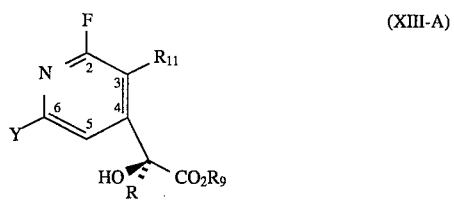

(XIII-A)

The compound of Formula (XIII) is then substituted at position 3 with a loweralkyl-ester or aryl-ester to provide the compounds of Formula (XIV). The substitution reaction may be accomplished by reacting the compound of Formula (XIII) with an alkali metal carboxylate such as for example, sodium acetate, potassium acetate, lithium acetate, and the like. Currently, sodium and potassium acetate are preferred. The reaction takes place in an organic solvent such as methyl ethyl ketone, at reflux. In the embodiment wherein the compounds of Formulas (XII) and (XIII) are diastereomerically enhanced, the resulting compounds of Formula (XIV) are similarly diastereomerically enhanced, and have the stereochemical orientation of Formula (XIV-A)

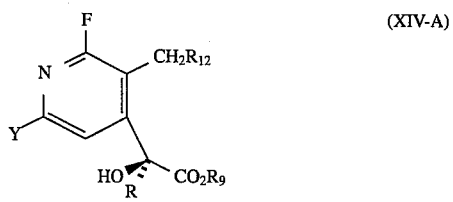

(XIV-A)

The final step of Scheme E is the formation of compound (III) from a compound of Formula (XIV) by hydrolysis. The chiral auxiliary is removed from the compound of Formula (XIV), the $C_3$ ester is cleaved and an ester ring is formed with the linkage at the position previously occupied by the chiral auxiliary. The cleavage of the esters and ester cyclization reaction may be carried out by hydrolyzing the compound of Formula (XIV) with aqueous inorganic base followed by treatment with dilute inorganic acid. The addition of aqueous inorganic base effects the ester hydrolysis, and the subsequent addition of dilute inorganic acid cyclizes the ester. Preferably, the aqueous inorganic base is sodium hydroxide. Preferably the inorganic acid is hydrochloric acid diluted to 3 Molar. The reaction is heated at reflux for approximately 36 hours. The reaction may be carried out in a polar solvent, such as methanol, ethanol, isopropanol, etc. Preferably the solvent is methanol. The reaction produces the compounds of Formula (III) in crystalline form, having a melting point between about 216°–218° C.

As noted above, when Y is halo in the compound of Formula (III), the compound may be hydrogenated by any suitable technique to produce compounds of Formula (III) wherein Y is H.

The following examples are provided to illustrate the present invention, and should not be construed as limiting thereof. In these examples, "LDA" means lithium diisopropylamide; "n-BuLi" means n-butyllithium, "THF" means tetrahydrofuran, "MgSO$_4$" means magnesium sulfate, "EtOAc" means ethyl acetate, "K$_2$CO$_3$" means potassium carbonate, "CCl$_4$" means carbon tetrachloride, "NaOH" means sodium hydroxide, "HCl" means hydrochloric acid, "MeOH" means methanol, "CH$_2$Cl$_2$" means methylene chloride, "M" means Molar, "mol" means mole, "mmol" means millimoles, "g" means grams, "mg" means milligrams, "L" means liters, "mL" means milliliters, "° C." means degrees Centrigrade, "min." means minutes, "mp" means melting point, and "plc" means preparative layer chromotagraphy.

EXAMPLE 1

2-Fluoro-4-iodo-3-(hydroxymethyl)pyridine

To a solution of LDA, freshly prepared from diisopropylamine (0.63 mL, 4.49 mmol) and n-BuLi (4.49 mmol) in THF (10 mL) at –78° C., is cannulated a solution of 2-fluoro-3-iodopyridine (1 g, 4.48 mmol) in 2 mL of THF, and the mixture is stirred for 1 hour at –78° C. under nitrogen. Ethyl formate (1.1 mL, 13.6 mmol) is added to the reaction mixture at –78° C. and stirring is continued for 30 min. The reaction is quenched with saturated sodium bicarbonate solution at –78° C. and allowed to warm to room temperature. Sodium borohydride (0.34 g, 8.99 mmol) is slowly added to the reaction mixture and then stirred for 30 min. The mixture is extracted with ethyl acetate. The combined ethyl acetate extracts are washed with brine, dried (MgSO$_4$) and concentrated in vacuo. The residue is purified by radial plc (silica gel, hexanes, 10% EtOAc/hexanes, 20% EtOAc/hexanes) to afford 708 mg (62 %) of the product as a white solid having a mp of 69°–70° C.

Elemental Analysis for C$_6$H$_5$FINO: theory: C 28.48, H 1.99, N 5.54; found: C 28.55, H 1.94, N 5.48. IR (KBr): cm$^1$3336, 1584, 1541, 1446, 1401, 1264, 1218, 1003, 870, 833,803,761,577. $^1$H NMR (CDCl$_3$): δ7.79–7.82 (d, 1H,J=5 Hz), 7.66–7.68 (d, 1H, J=5 Hz), 4.82–4.86 (d, 2H, J=7 Hz), 1.99–2.04 (t, 1H, J=14 Hz). $^{13}$C NMR (CDCl$_3$): δ 162.29, 159.05, 147.30, 147.09, 132.79, 132.73,126.14, 125.73, 114.21, 62.24.

EXAMPLE 2

2-Fluoro-4-iodo-3-(methoxymethoxymethyl)pyridine

To a stirred solution of 2-fluoro-4-iodo-3-(hydroxymethyl)-pyridine (679 mg, 2.68 mmol) in 10 mL of CH$_2$Cl$_2$ at 0° C. is added diisopropylethylamine (2.34 mL, 13.4 retool), 4-dimethylaminopyridine (33 rag, 0.270 mmol), and chloromethyl methyl ether (0.61 mL, 8.03 mmol) successively under nitrogen. The reaction mixture is slowly warmed to room temperature and stirred for 20 hours. After removal of the solvent in vacuo, the residue is purified by radial plc (silica gel, hexanes, 5% EtOAc/hexanes) to give 699 mg (88%) of the product as a colorless oil.

Analysis: HRMS exact mass calculated for C$_8$H$_9$FINO$_2$ 296.9662 (M+), found 296.9664. IR (CHCl$_3$): cm$^{-1}$ 3008, 2945, 1585, 1550, 1448, 1410, 1380, 1149, 1102, 1040, 944, 876. $^1$H NMR (CDCl$_3$): δ 7.79–7.82 (d, 1H, J= 5 Hz), 7.66–7.69 (d, 1H, J=5 Hz), 4.75 (s, 2H), 4.72 (s, 2H), 3.43 (s, 3H). $^{13}$C NMR (CDCl$_3$):δ 162.48, 159.25, 147.44, 147.22, 132.61,132.56, 123.82, 123.40, 114.96, 96.41, 66.19, 55.49.

EXAMPLE 3

(1R,2S)-trans-2-(α-Cumyl)cyclohexyl-(S)-2-(hydroxy)-2-(2'-fluro- 3'-methoxymethoxymethyl-4'-pyridyl) butyrate To a vigorously stirred solution of the iodide prepared in Example 2 (73 mg, 0.246 mmol) in 1.5 mL of THF at –78° C. is added n-BuLi (2.41M, 0.11 mL, 0.258 mmol), and the mixture is stirred for 1 min. A solution of (–)-trans-2-(α-cumyl)cyclohexyl 2-ketobutyrate (82 mg, 0.271 mmol) in 0.5 mL of THF is cannulated into the reaction mixture and stirred for 15 min. under nitrogen at –78° C. The reaction is allowed to warm to room temperature for 15 min, quenched with saturated sodium bicarbonate solution, and extracted with ether. Combined ether extracts are dried (K$_2$CO$_3$) and concentrated in vacuo. The residue is purified by radial plc (silica gel, 2% EtOAc/hexanes, 5% EtOAc/hezanes, 10% EtOAc/hexanes) to provide 64 mg (55 %) of the product as a colorless oil.

Analysis: HRMS exact mass calculated for [C$_{27}$H$_{36}$FNO$_5$+H] 74.2656 [(M+H)+], found 474.2670. IR (CHCl$_3$): cm$_{-1}$ 2939, 2863, 1715, 1601, 1551, 1498 1467, 1448, 1410, 1391, 1368, 1288. $_1$H NMR (CDCl$_3$): δ 8.10–8.13 (d, 1H, J=5 Hz), 7.12–7.24 (m, 5H), 7.06–7.09 (d, 1H, J=5 Hz) 4.75–4.86 (m, 3H), 4.65–4.71 (m, 2H), 3.75 (s, 1H), 3.41 (s, 3H), 2.06–2.13 (t, 1H, J=19 Hz), 1.00–1.94 (m, 16H), 0.80–0.85 (t, 3H, J=15 Hz). $_{13}$C NMR (CDCl$_3$): δ 172.34, 165.24, 162.07, 154.45, 151.03, 146.58, 146.37, 128.16, 125.38, 125.31, 120.31, 118.49, 118.11, 96.38, 79.97, 78.47, 59.91, 55.62, 49.95, 39.91, 32.34, 31.93, 27.48, 27.11, 26.05, 25.55, 24.31, 7.75.

EXAMPLE 4

2-Fluoro-4-iodo-3-methylpyridine (6)

To a solution of LDA, freshly prepared from diisopropylamine (0.126 mL, 0.899 mmol) and n-BuLi (0.899 mmol), in THF (2 mL) at –78° C. is cannulated a solution of 2-fluoro-3-iodopyridine (200 mg, 0.897 mmol) in 0.4 mL of THF, and the mixture is stirred for 1 hour at –78° C. under nitrogen. Iodomethane (0.17 mL, 2.73 mmol) is added neat and the mixture is stirred for 30 min. at –78° C. The mixture is quenched with saturated sodium bicarbonate solution at –78° C. and then extracted with ether. Combined ether extracts are dried (MgSO$_4$) and concentrated in vacuo. The residue is purified by radial plc (silica gel, hexanes) to give 154 mg (72%) of product as an off-white solid having amp of 90–91 ° C.

EXAMPLE 5

(1R,2S)-trans-2-(α-Cumyl)cyclohexyl-(S)-2-(hydroxy)-2(2'-fluoro- 3'-methyl-4'-pyridyl)butyrate To a vigorously stirred solution of 2-fluoro-4-iodo-3-methylpyridine (100 mg, 0.422 mmol), prepared according to Example 4, in 2.5 mL of THF at –78° C. under nitrogen is added n-BuLi (2.36M, 0.19 mL, 0.443 mmol) and the mixture is stirred for 1 min. A solution of (−)(1R,2S)-trans-2-(α-cumyl)cyclohexyl 2-ketobutyrate (140 mg, 0.463 mmol) in 0.8 mL of THF is added to the reaction mixture. After stirring 15 min. at −78° C., the reaction mixture is allowed to warm to room temperature for 15 min. The mixture is quenched with saturated sodium bicarbonate solution and extracted with ether. The combined ether extracts are dried ($K_2CO_3$) and concentrated in vacuo. The residue is purified by radial plc (silica gel, 1% acetone/hexanes, 2% acetone/hexanes) to give 140 mg (80%) of product as a colorless oil (94% de as determined by 500 MHz $^1H$ NMR analysis). The other diastereomer could not be separated by radial plc.

Analysis: HRMS exact mass calculated for $C_{25}H_{32}FNO_3$ 413.2366 (M+), found 413.2376. IR ($CHCl_3$): $cm^{-1}$ 2963, 2862, 1717, 1607, 1407, 1098, 1015. $^1H$ NMR ($CDCl_3$): δ 7.98–8.00 (d, 1H, J=5 Hz), 7.15–7.22 (m, 5H), 7.00–7.03 (d, 1H, J=5 Hz), 4.76–4.85 (m, 1H), 2.91 (bs, 1H), 2.23 (s, 3H), 1.02–2.15 (m, 17H), 0.79–0.85 (t, 3H, J=15 Hz). $_{13}C$ NMR ($CDCl_3$): δ 172.76, 164.87, 161.74, 152.52, 152.47, 151.15, 143.85, 143.64, 128.11, 125.23, 125.14, 119.57, 119.52, 119.00, 118.58, 78.73, 49.55, 39.71, 32.19, 30.24, 28.16, 6.98, 25.51, 25.22, 24.29, 11.99, 7.62.

EXAMPLE 6

(1R,2S)-trans-2-(α-Cumyl)cyclohexyl-(S)-2-(hydroxy)-2-(2'-fluoro-3'-bromomethyl-4'-pyridyl)butyrate A mixture of the hydroxyester (92 mg, 0.223 mmol) prepared according to Example 5, recrystallized N-bromosuccinimide (44 mg, 0.247 mmol) and dibenzoyl peroxide (2.5 mg) in 2 mL of $CCl_4$ under nitrogen is heated at reflux for 4 hours by means of a 60-watt light bulb. The mixture is cooled in an ice bath and filtered through Celite. The residue is washed with $CCl_4$, and the filtrate is concentrated in vacuo. The crude product is purified by radial plc (silica gel, 5% EtOAc/pentane) to give 81 mg (74%) of product as a colorless oil.

Analysis: HRMS exact mass calculatd for $C_{25}H_{31}BrFNO_3$ 491.1472 (M+), found 491.1456. IR($CHCl_3$): $cm^{-1}$ 2940, 2861, 1719, 1597, 1551, 1499, 1462, 1406, 1144. $^1H$ NMR ($CDCl_3$): δ 8.07–8.10 (d, 1H, J=5 Hz), 7.10–7.24 (m, 5H), 7.04–7.06 (d, 1H, J=5 Hz), 4.74–4.89 (m, 3H) 2.95 (s, 1H), 2.14–2.23 (m, 1H), 1.05–1.98 (m, 16 H), 0.79–0.85 (t, 3H, J=15 Hz). $^{13}C$ NMR ($CDCl_3$): δ 171.76, 164.87, 161.67, 152.41, 151.26, 146.41, 146.19, 128.14, 125.33, 125.08, 120.27, 119.91, 119.53, 80.43, 79.07, 49.75 39.69, 32.47, 31.96, 28.60, 26.92, 25.54, 24.70, 24.32, 22.87, 7.76.

EXAMPLE 7

(1R,2S)-trans-2-(α-Cumyl)cyclohexyl-(S)-2-(hydroxy)2-(2'-fluoro-3'-acetoxymethyl-4'-pyridyl)butyrate To a stirred solution of the bromo compound prepared according to Example 6 (70 mg, 0.142 mmol) in 2 mL of methyl ethyl ketone is added potassium acetate (42 mg, 0.428 mmol). The mixture is heated at reflux under nitrogen for 15 min. The reaction mixture is cooled and solvent is removed by rotary evaporator. The residue is dissolved in anhydrous ether and filtered through Celite. The solid is washed with anhydrous ether, and the filtrate is concentrated in vacuo. The crude product is purified by radial plc (silica gel, 10% EtOAc/hexanes) to give 64 mg (96%) of product as a colorless oil.

Analysis: HRMS exact mass calculated for $C_{27}H_{34}FNO_5$ 471.2421 (M+), found 471.2410. IR ($CHCl_3$): $cm^{-1}$ 2939, 2864, 1728, 1606, 1553, 1497, 1464, 1412, 1386, 1367. $^1H$ NMR ($CDCl_3$): δ 8.13–8.15 (d, 1H, J=5 Hz), 7.14–7.24 (m, 5H), 7.05–7.08 (d, 1H, J=5 Hz), 5.32 (s, 2H) 4.78–4.87 (m, 1H), 314 (s, 1H), 2.10–2.23 (m, 1H), 2.06 (s, 3H), 1.03–1.90 (m, 16H), 0.77–0.83 (t,3H, J=15 Hz). $^{13}C$ NMR ($CDCl_3$): δ 172.18, 170.42, 165.37, 162.18, 154.17, 154.13, 151.22, 146.94, 146.73, 128.11, 125.30, 125.12, 120.24, 116.91, 116.53, 79.63, 78.87, 57.36, 49.64, 39.68, 32.32, 31.96, 28.45, 26.92, 25.51, 24.84, 24.28, 20.66, 7.65.

EXAMPLE 8

7-Oxopyrido [5,4-c]-2-oxo-(S)-3-ethyl-3-hydroxy-3, 6-dihydropyran

A mixture of acetoxy compound prepared according to Example 7 (93 mg, 0.197 mmol) in a 2 mL of 1:1 ethanol/2N NaOH is heated at 80°–90° C. in air for 12 hours. Most of the ethanol is removed under reduced pressure. The residue is diluted with water (0.5 mL) and extracted with ether. The chiral auxiliary,(−)-trans-2-(α-cumyl)cyclohexanol is recovered in 95% yield after evaporation of the ether extracts. The basic aqueous layer is concentrated in vacuo. The residue is treated with 2 mL of 3N HCl and heated at reflux in air for 21 hours. The reaction mixture is cooled to room temperature and concentrated in vacuo. The crude product is purified by radial plc (silica gel, 5% MeOH/$CH_2Cl_2$) to give 30 mg (73%) of the DE ring intermediate as a white solid having amp of 228°–230° C. (dec); $[\alpha]_D^{25}$ +126.14° (c 0.70, MeOH).

EXAMPLE 9

7-Oxopyrido [5,4-cl-2-oxo-(S)-3-ethyl-3-hydroxy-3, 6-dihydropyran

A mixture of methoxymethoxymethyl compound prepared according to Example 3 (64 mg, 0.135 mmol) in 5 mL of 3N HCl is heated at reflux for 11 hours in air. The reaction mixture is cooled to room temperature and extracted with 10% MeOH/$CH_2Cl_2$. The combined organic extracts are dried ($MgSO_4$) and concentrated in vacuo. The chiral auxiliary, (−)-trans-2-(α-cumyl)cyclohexanol, is decomposed during hydrolysis. The residue is purified by radial plc (silica gel, 5% MeOH/$CHCl_3$) to give 11 mg (39%) of the DE ring intermediate as a white solid having amp of 228°–230° C. (dec); $[\alpha]_D^{24}$ +120°(c 0.34, MeOH).

The foregoing is illustrative of the present invention and is not to be construed as limiting thereof. The invention is defined by the following claims, with equivalents of the claims to be included therein.

That which is claimed is:

1. A method of making a compound of Formula (III)

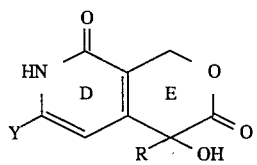
(III)

wherein R is loweralkyl, and Y is H or halogen; by hydrolyzing a compound of Formula (X)

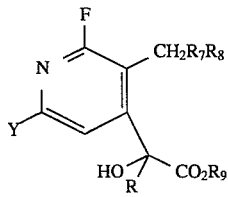
(X)

wherein $R_7$ is loweralkoxy, $R_8$ is loweralkoxy and the $R_9$ moiety has a configuration that forces R and the —OH group of the compound (X) to take a first stereochemical orientation about the chiral carbon at position 7 by sterically hindering the formation of an opposite, second stereochemical orientation about the chiral carbon at position 7;

in an aqueous solution under heat with an inorganic acid to yield the compound of Formula (III).

2. The method according to claim 1, wherein said compound of Formula (X) is prepared by reacting a compound of Formula (VIII)

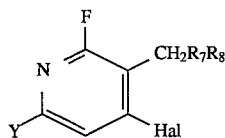
(VIII)

wherein Hal is halogen; with a base of the Formula $A^+B^{31}$, wherein $A^+$ is an inorganic cation, and $B^-$ is an organic anion, to form a first intermediate, then stereospecifically adding to the first intermediate, an α-ketoester of Formula (IX)

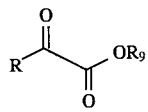
(IX)

at a temperature below 0° C. to yield the compound of Formula (X).

3. The method according to claim 2, wherein said compound of Formula (VIII) is prepared by reacting a compound of Formula (VII)

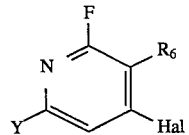
(VII)

wherein $R_6$ is loweralkylhydroxy;
with diisopropylethylamine, 4-dimethylaminopyridine and chloromethyl methyl ether to yield the compound of Formula (VIII).

4. The method according to claim 3, wherein said compound of Formula (VII) is prepared by reacting a compound of Formula (VI)

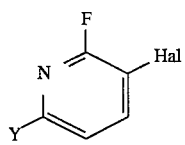
(VI)

with lithium diisopropylamide, ethyl formate and sodium borohydride at a temperature below 0° C. to yield a compound of Formula (VII).

5. The method according to claim 1, wherein $R_9$ is optically pure, and wherein R and the —OH group of the compound of Formula (X) have the stereochemical orientation of Formula (X-A)

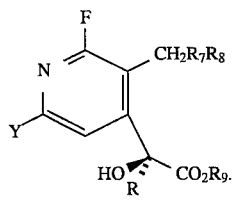
(X-A)

6. The method according to claim 1, wherein $R_9$ comprises a moiety of Formula (IX-B):

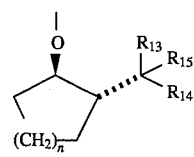
(IX-B)

wherein n is 1, 2, or 3, $R_{13}$ is a $C_1$–$C_4$ alkyl group and $R_{14}$ is the same as $R_{13}$, or $R_{13}$ and $R_{14}$ together form cyclopentane or cyclohexane, and $R_{15}$ is
(a) phenyl substituted 1 to 5 times with $C_3$–$C_7$ secondary alkyl or $C_4$–$C_7$ tertiary alkyl, or
(b) selected from the group consisting of naphthyl, anthryl, and phenanthryl optionally substituted 1 to 5 times with $C_3$–$C_7$ secondary alkyl or C4–$C_7$ tertiary alkyl.

7. The method according to claim 6, wherein $R_{13}$ and $R_{14}$ are both methyl or ethyl, and $R_{15}$ is phenyl optionally substituted from 1 to 3 times at the 3, 4, or 5 position with isopropyl or t-butyl.

8. The method according to claim 1, wherein R is ethyl.
9. The method according to claim 1, wherein Y is H.
10. The method according to claim 2, wherein Hal is iodo.
11. A method of making a compound of Formula (X)

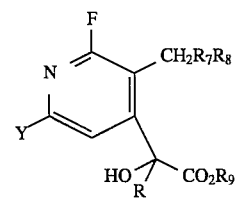
(X)

wherein Y is H or halogen, R is loweralkyl, $R_7$ is loweralkoxy, $R_8$ is loweralkoxy, and the $R_9$ moiety has a configuration that forces R and the —OH group of the compound (X) to take a first stereochemical orientation about the chiral carbon at position 7 by sterically hindering the formation of an opposite, second stereochemical orientation about the chiral carbon at position 7;

comprising reacting a compound of Formula (VIII)

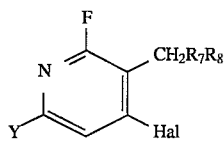

(VIII)

wherein Hal is halogen;
with a base of the Formula $A^+B^-$, wherein $A^+$ is an inorganic cation, and $B^-$ is an organic anion, to form a first intermediate, then stereospecifically adding to the first intermediate, an α-ketoester of Formula (IX)

(IX)

at a temperature below 0° C. to yield the compound of Formula (X).

12. The method according to claim 11, wherein $R_9$ is optically pure, and wherein R and the —OH group of the compound of Formula (X) have the stereochemical orientation of Formula (X-A)

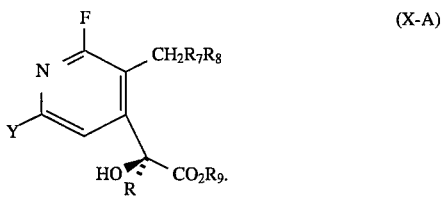

(X-A)

13. The method according to claim 11, wherein $R_9$ comprises a moiety of Formula (IX-B):

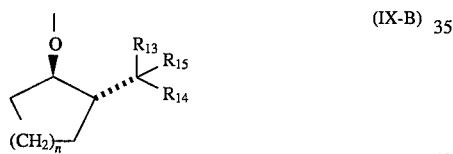

(IX-B)

wherein n is 1, 2, or 3, $R_{13}$ is a $C_1$–$C_4$ alkyl group and $R_{14}$ is the same as $R_{13}$, or $R_{13}$ and $R_{14}$ together form cyclopentane or cyclohexane, and $R_{15}$ is (a) phenyl substituted 1 to 5 times with $C_3$–$C_7$ secondary alkyl or $C_4$–$C_7$ tertiary alkyl, or (b) selected from the group consisting of naphthyl, anthryl, and phenanthryl optionally substituted 1 to 5 times with $C_{13}$–$C_7$ secondary alkyl or $C_4$–$C_7$ tertiary alkyl.

14. The method according to claim 13, wherein $R_{13}$ and $R_{14}$ are both methyl or ethyl, and $R_{15}$ is phenyl optionally substituted from 1 to 3 times at the 3, 4, or 5 position with isopropyl or t-butyl.

15. The method according to claim 11, wherein R is ethyl.

16. The method according to claim 11, wherein Hal is iodo.

17. The method according to claim 11, wherein $B^-$ is n-butyl.

18. A compound of Formula (X)

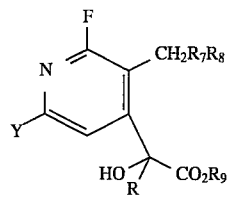

(X)

wherein Y is H or halogen, R is loweralkyl, $R_7$ is loweralkoxy, $R_8$ is loweralkoxy, and the $R_9$ moiety has a configuration that forces R and the —OH group of the compound (X) to take a first stereochemical orientation about the chiral carbon at position 7 by sterically hindering the formation of an opposite, second stereochemical orientation about the chiral carbon at position 7.

19. The compound accoring to claim 18, wherein $R_9$ is optically pure, and wherein R and the —OH group of the compound of Formula (X) have the stereochemical orientation of Formula (X-A)

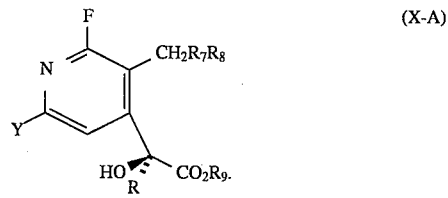

(X-A)

20. The compound according to claim 18, wherein $R_9$ comprises a moiety of Formula (IX-B):

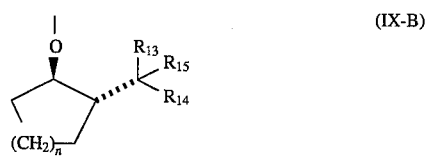

(IX-B)

wherein n is 1, 2, or 3, $R_{13}$ is a $C_1$–$C_4$ alkyl group and $R_{14}$ is the same as $R_{13}$, or $R_{13}$ and $R_{14}$ together form cyclopentane or cyclohexane, and $R_{15}$ is (a) phenyl substituted 1 to 5 times with $C_3$–$C_7$ secondary alkyl or $C_4$–$C_7$ tertiary alkyl, or (b) selected from the group consisting of naphthyl, anthryl, and phenanthryl optionally substituted 1 to 5 times with $C_3$–$C_7$ secondary alkyl or $C_4$–$C_7$ tertiary alkyl.

21. The compound according to claim 20, wherein $R_{13}$ and $R_{14}$ are both methyl or ethyl, and $R_{15}$ is phenyl optionally substituted 1 to 3 times at the 3, 4, or 5 position with isopropyl or t-butyl.

22. The compound according to claim 18, wherein R is ethyl.

* * * * *

UNITED STATES PATENT AND TRADEMARK OFFICE
CERTIFICATE OF CORRECTION

PATENT NO. : 5,496,952  Page 1 of 2
DATED : March 5, 1996
INVENTOR(S) : Daniel L. Comins It is certified that error appears in the above-identified patent and that said Letters Patent is hereby corrected as shown below:

Column 4, line 59, please correct "-50°C" to read -- -0°C --.

Column 5, line 32, please add --compound-- after from.

Column 5, line 60, please correct " R9 " to read -- $R_9$ --.

Column 6, line 12, please correct "$R_4$" to read -- $R_{14}$ --.

Column 6, line 13, please correct "$R_3$" to read -- $R_{13}$ --.

Column 9, Example 2, line 62, please correct "retool)" to read -- mmol --.

Column 9, Example 2, line 63, please correct "rag" to read -- mg --.

Column 10, Example 3, line 32, please correct "74,2656" to read -- 474.2656 --.

Column 10, Example 3, line 33, please correct "$cm_{-1}$" to read -- $cm^{-1}$ --.

Column 10, Example 3, line 34, please correct "$_1H$" to read -- $^1H$ --.

Column 10, Example 3, line 38, please correct "$_{13}C$" to read -- $^{13}C$ --.

Column 10, Example 4, line 58, please correct "amp" to read -- a mp --.

UNITED STATES PATENT AND TRADEMARK OFFICE
CERTIFICATE OF CORRECTION

PATENT NO. : 5,496,952
DATED : 05 March 1996
INVENTOR(S) : Daniel L. Comins It is certified that error appears in the above-identified patent and that said Letters Patent is hereby corrected as shown below:

Column 11, Example 5, line 20, please correct "$_{13}$C" to read --$^{13}$C--.

Column 11, Example 5, line 25, please correct "6.98" to read --26.98--.

Column 12, Example 9, line 59, please correct "amp" to read --a mp--.

Column 13, claim 2, line 38, please start new paragraph with the word "with".

Column 13, claim 2, line 38, please correct "B$^{31}$" to read --B$^-$--.

Column 15, claim 13, line 48, please correct "C$_{13}$" to read --C$_3$--.

Signed and Sealed this

Twenty-third Day of July, 1996

BRUCE LEHMAN

*Attest:*

*Attesting Officer*         *Commissioner of Patents and Trademarks*